United States Patent
Kogai et al.

(10) Patent No.: US 8,322,218 B2
(45) Date of Patent: Dec. 4, 2012

(54) SURFACE ACOUSTIC WAVE ELEMENT AND EQUIPMENT FOR MEASURING CHARACTERISTICS OF LIQUID MATERIAL

(75) Inventors: Takashi Kogai, Mitaka (JP); Hiromi Yatsuda, Mitaka (JP)

(73) Assignee: Japan Radio Co., Ltd., Tokyo (JP)

( * ) Notice: Subject to any disclaimer, the term of this patent is extended or adjusted under 35 U.S.C. 154(b) by 257 days.

(21) Appl. No.: 12/743,753

(22) PCT Filed: Nov. 17, 2008

(86) PCT No.: PCT/JP2008/070879
§ 371 (c)(1),
(2), (4) Date: May 19, 2010

(87) PCT Pub. No.: WO2009/066640
PCT Pub. Date: May 28, 2009

(65) Prior Publication Data
US 2010/0236322 A1 Sep. 23, 2010

(30) Foreign Application Priority Data

Nov. 20, 2007 (JP) ................................. 2007-300603

(51) Int. Cl.
*G01N 29/00* (2006.01)
*H01L 11/08* (2006.01)
*H01L 41/053* (2006.01)
(52) U.S. Cl. ..................... 73/594; 73/53.01; 310/313 C; 310/323.21
(58) Field of Classification Search ........... 73/73, 53.01, 73/594, 597, 649, 655; 310/313 C, 313 R, 310/323.21
See application file for complete search history.

(56) References Cited

U.S. PATENT DOCUMENTS

| | | | | |
|---|---|---|---|---|
| 3,699,482 A | * | 10/1972 | Ash et al. | 333/150 |
| 3,805,195 A | * | 4/1974 | Miller | 333/150 |
| 5,163,435 A | * | 11/1992 | Soldner et al. | 600/447 |
| 5,235,235 A | | 8/1993 | Martin et al. | |
| 7,154,206 B2 | * | 12/2006 | Shimada et al. | 310/313 R |
| 7,513,022 B2 | * | 4/2009 | Shimada et al. | 29/25.35 |

FOREIGN PATENT DOCUMENTS

| | | |
|---|---|---|
| JP | 2-6728 | 1/1990 |
| JP | 10-270975 | 10/1998 |
| JP | 11-211705 | 8/1999 |
| JP | 3481298 | 10/2003 |
| JP | 2008-267968 | 11/2008 |
| WO | WO 2006/010206 | 2/2006 |

OTHER PUBLICATIONS

J. Kondoh et al., "Development of Surface Acoustic Wave Liquid Sensing System and Application for Japanese Tea Measurements", 2001 IEEE International Frequency Control Symposium and PDA Exhibition, pp. 497-501, Jun. 8, 2001.
Office Action issued on Sep. 28, 2012 in Canadian Patent Application No. 2706059.

* cited by examiner

*Primary Examiner* — J M Saint Surin
(74) *Attorney, Agent, or Firm* — Cozen O'Connor

(57) ABSTRACT

A surface acoustic wave device having electrodes disposed on a piezoelectric substrate, comprising a sealing member having a peripheral wall disposed on the piezoelectric substrate in surrounding relation to the electrodes, and a top plate covering the peripheral wall; and a sealing stiffener disposed on the piezoelectric substrate in facing relation to a liquid material imposed on the piezoelectric substrate and which extends parallel to a portion of the peripheral wall.

10 Claims, 8 Drawing Sheets

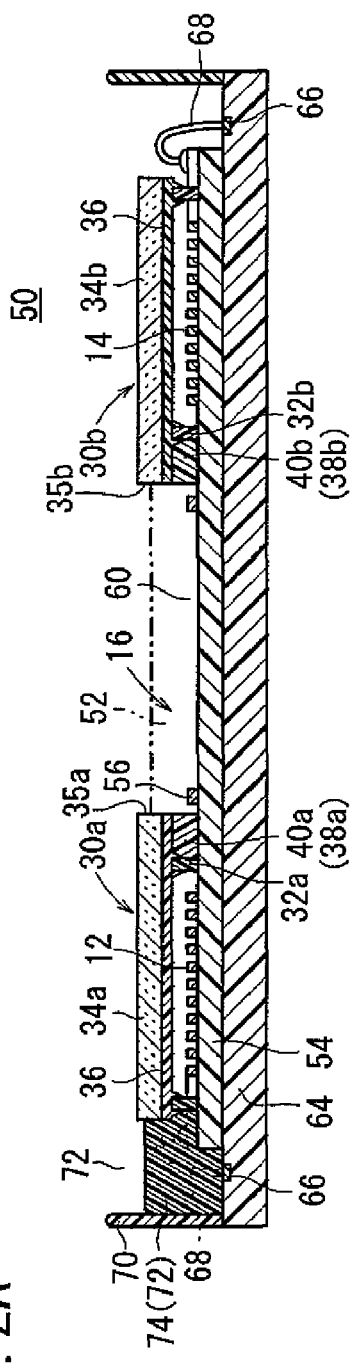
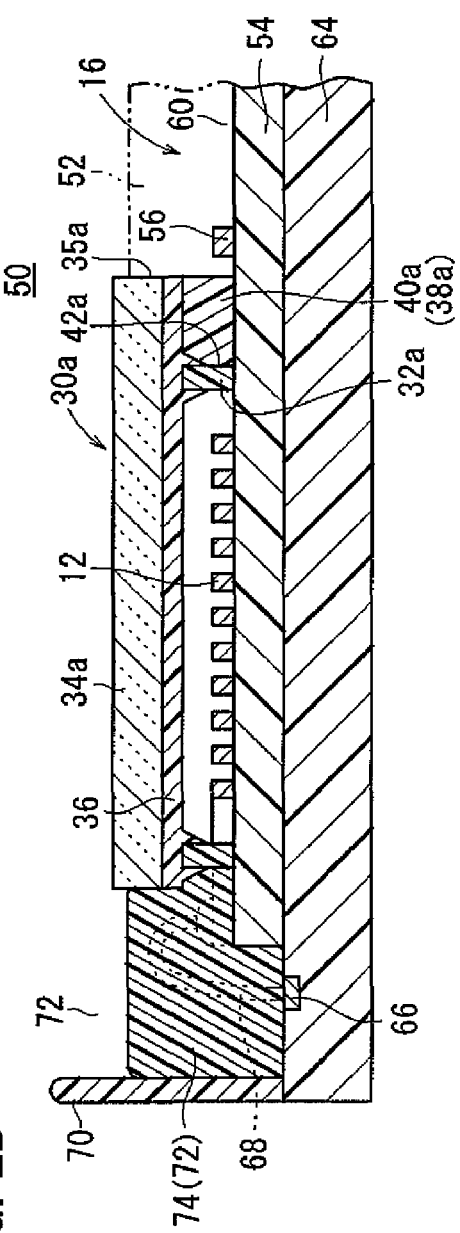
FIG. 2A
FIG. 2B

SURFACE ACOUSTIC WAVE ELEMENT AND EQUIPMENT FOR MEASURING CHARACTERISTICS OF LIQUID MATERIAL

RELATED APPLICATIONS

This is a U.S. National Phase Application under 35 U.S.C. 371 of International Application PCT/JP2008/070879, filed on Nov. 17, 2008.

This application claims the priority of Japanese Application No. 2007-300603 filed on Nov. 20, 2007, the entire content of which is hereby incorporated by reference.

TECHNICAL FIELD

The present invention relates to a surface acoustic wave device (element) having sealed electrodes disposed on a piezoelectric substrate, as well as to a liquid material property (characteristic) measuring apparatus (equipment) incorporating such a surface acoustic wave device therein.

BACKGROUND ART

Generally, a surface acoustic wave device comprises a piezoelectric substrate, together with an input electrode and an output electrode, which comprise comb-tooth electrode fingers disposed on the piezoelectric substrate. When an electric signal is input to the input electrode of the surface acoustic wave device, an electric field is generated between the electrode fingers, and surface acoustic waves are excited due to the piezoelectric effect and propagated over the piezoelectric substrate. There has been under research a surface acoustic wave sensor for detecting various substances and measuring properties thereof, which incorporates therein a surface acoustic wave device that utilizes shear horizontal surface acoustic waves (SH-SAW) among the excited surface acoustic waves referred to above. Shear horizontal surface acoustic waves are displaced in a direction perpendicular to the direction of propagation of surface acoustic waves (Japanese Patent No. 3481298).

Operation of the surface acoustic wave sensor utilizes the fact that output signals output from the output electrode have different characteristics when a region of the piezoelectric substrate where a liquid material to be measured is placed is electrically open compared with when the same region of the piezoelectric substrate is electrically short-circuited. More specifically, the output signal produced when the region of the piezoelectric substrate is open is subjected to both electrical and mechanical interactions, whereas the output signal produced when the region of the piezoelectric substrate is short-circuited is subjected only to mechanical interactions. Therefore, physical properties of the liquid material, such as a dielectric constant, electric conductivity, etc., can be determined by canceling out mechanical interactions, and then extracting electrical interactions from the output signals.

For measuring physical properties of a liquid material with the surface acoustic wave sensor, there are instances where the surface acoustic wave sensor is immersed in the liquid material. In such applications, the electrodes of the surface acoustic wave device of the surface acoustic wave sensor are sealed by sealing members in order to prevent the electrodes from becoming short-circuited by the liquid material.

If the sealing members are disposed on the propagation path of the surface acoustic waves, then since the thickness of the sealing members in the direction of propagation is determined by propagation characteristics of the surface acoustic waves, the sealing member must be formed with great accuracy. Furthermore, the sealing members that seal the electrodes may become peeled off from the piezoelectric substrate upon elapse of a certain period of time, with the result that the liquid material may find its way into gaps between the peeled-off sealing members and the piezoelectric substrate, thus tending to short-circuit the electrodes.

DISCLOSURE OF THE INVENTION

The present invention has been made in view of the above problems. It is an object of the present invention to provide a surface acoustic wave device, which prevents electrodes from becoming short-circuited even when the surface acoustic wave device is immersed in a liquid material. The present invention also has the object of providing a liquid material property measuring apparatus incorporating such a surface acoustic wave device therein for measuring physical properties of a liquid material.

According to the present invention, there is provided a surface acoustic wave device having electrodes disposed on a piezoelectric substrate, comprising a sealing member having a peripheral wall disposed on the piezoelectric substrate in surrounding relation to the electrodes, and a top plate covering the peripheral wall. Further, a sealing stiffener is disposed on the piezoelectric substrate in facing relation to a liquid material imposed on the piezoelectric substrate and which extends parallel to a portion of the peripheral wall.

According to the present invention, the sealing stiffener prevents liquid material from coming into contact with the peripheral wall, prevents the peripheral wall from being peeled off from the piezoelectric substrate, and prevents liquid material from being applied to the electrodes.

According to another aspect of the present invention, there is provided a surface acoustic wave device having electrodes disposed on a piezoelectric substrate, comprising a sealing member having a peripheral wall disposed on the piezoelectric substrate in surrounding relation to the electrodes, a first wall disposed on the piezoelectric substrate in facing relation to a liquid material imposed on the piezoelectric substrate and which extends parallel to a portion of the peripheral wall, and a top plate covering the peripheral wall and the first wall.

The first wall and the peripheral wall jointly make up a double protective wall, which prevents liquid material from coming into contact with the peripheral wall, prevents the peripheral wall from being peeled off from the piezoelectric substrate, and prevents liquid material from being applied to the electrodes. Furthermore, a sealing stiffener may be provided, which fills the space between the first wall and a wall portion of the peripheral wall that faces the first wall.

The peripheral wall is made of a photosensitive resin. Therefore, it is possible for the peripheral wall to have a desired thickness in the direction of propagation of the surface acoustic waves, thereby preventing propagation characteristics of the surface acoustic waves from becoming degraded.

According to still another aspect of the present invention, there is provided a liquid material property measuring apparatus including the above surface acoustic wave device, wherein the electrodes include an input electrode and an output electrode, each of which is sealed by the sealing member, and wherein the liquid material property measuring apparatus determines physical properties of the liquid material, which is imposed on a transmission path disposed between the input electrode and the output electrode. The surface acoustic wave device includes a first surface acoustic wave device having a first propagation path disposed between first input and output electrodes, and a second surface acoustic wave device having a second propagation path disposed between second input and output electrodes, and having different amplitude and phase characteristics from the first propagation path. Accordingly, the surface acoustic wave device can determine physical properties of a liquid material that is imposed on the first propagation path and the second propagation path. The first input electrode and the second input electrode may be comprised of the same electrode.

According to the present invention, a sealing stiffener prevents liquid material from coming into contact with the peripheral wall, prevents the peripheral wall from being peeled off from the piezoelectric substrate, and further prevents liquid material from being applied to the electrodes.

The peripheral wall and a first wall facing the liquid material and which extends parallel to a portion of the peripheral wall, thereby jointly making up a double protective wall that prevents liquid material from coming into contact with the peripheral wall, prevents the peripheral wall from being peeled off from the piezoelectric substrate, and prevents liquid material from being applied to the electrodes. Furthermore, a sealing stiffener, which fills a space between the first wall and a wall portion of the peripheral wall that faces the first wall, is effective to reliably prevent liquid material from being applied to the electrodes.

The peripheral wall is made of a photosensitive resin, thus making it possible for the peripheral wall to have a desired thickness in the direction of propagation of the surface acoustic waves, and preventing propagation characteristics of the surface acoustic waves from becoming degraded.

In the liquid material property measuring apparatus including the above surface acoustic wave device, the electrodes include an input electrode and an output electrode, each of which is sealed by the sealing member. The liquid material property measuring apparatus determines physical properties of the liquid material, which is imposed on a transmission path disposed between the input electrode and the output electrode.

BRIEF DESCRIPTION OF THE DRAWINGS

FIG. 2A is a partial end view taken along line IIA-IIA of FIG. 1, and FIG. 2B is a partial enlarged view of FIG. 2A;

BEST MODE FOR CARRYING OUT THE INVENTION

Figure 1:
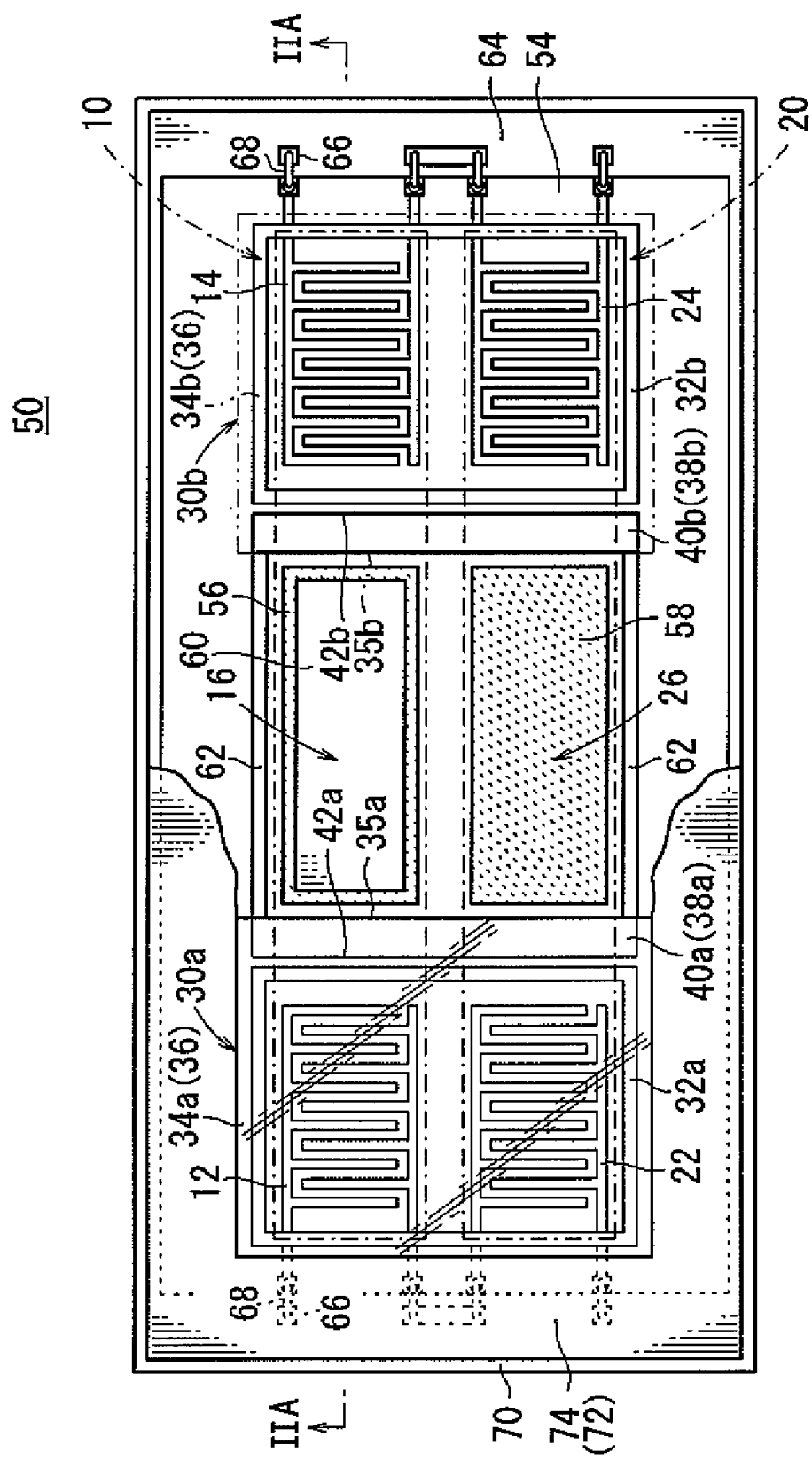
FIG. 1 is a plan view of a liquid material property measuring apparatus according to a first embodiment of the present invention.

A first embodiment of the present invention will be described below with reference to the drawings. FIG. 1 is a plan view of a liquid material property measuring apparatus 50 according to the first embodiment of the present invention. FIG. 2A is a partial end view taken along line IIA-IIA of FIG. 1, and FIG. 2B is a partial enlarged view of FIG. 2A.

As shown in FIG. 1, the liquid material property measuring apparatus 50 comprises a first surface acoustic wave device 10 and a second surface acoustic wave device 20. The first surface acoustic wave device 10 has an input electrode 12 and an output electrode 14, with a first propagation path 16 disposed between the input electrode 12 and the output electrode 14. The second surface acoustic wave device 20 has an input electrode 22 and an output electrode 24, with a second propagation path 26 disposed between the input electrode 22 and the output electrode 24.

The input electrode 12 and the input electrode 22 comprise comb-tooth electrodes for exciting surface acoustic waves on the basis of electric signals input thereto from an oscillator, not shown. The output electrode 14 and the output electrode 24 comprise comb-tooth electrodes for receiving surface acoustic waves excited by and propagated from the input electrode 12 and the input electrode 22.

The input electrode 12 and the input electrode 22 are sealed by a sealing member 30a, and the output electrode 14 and the output electrode 24 are sealed by a sealing member 30b. The sealing members 30a, 30b serve to prevent an object 52 to be measured, which is in the form of a liquid material, from being applied to the comb-tooth electrodes when the physical properties of the object 52 are measured.

The sealing member 30a comprises a peripheral wall 32a and a top plate 34a. The peripheral wall 32a is disposed on a piezoelectric substrate 54 in surrounding relation to the input electrodes 12, 22. The top plate 34a is bonded by an adhesive 36 to the upper end of the peripheral wall 32a in covering relation to the peripheral wall 32a. The top plate 34a is bonded to the upper end of the peripheral wall 32a substantially parallel to the piezoelectric substrate 54. The top plate 34a extends from the input electrodes 12, 22 and toward the first propagation path 16 and the second propagation path 26, with a gap 38a being defined between an end 35a of the top plate 34a and the piezoelectric substrate 54. The gap 38a is filled with a sealing stiffener 40a, which is applied to a wall portion 42a of the peripheral wall 32a that faces the object 52 imposed on the piezoelectric substrate 54. As with the sealing member 30a, the sealing member 30b comprises a peripheral wall 32b and a top plate 34b. A gap 38b defined between an end 35b and the piezoelectric substrate 54 is filled with a sealing stiffener 40b, which is applied to a wall portion 42b of the peripheral wall 32b. The sealing stiffeners 40a, 40b are disposed on the piezoelectric substrate 54, which faces the object 52 imposed on the first propagation path 16 and the second propagation path 26.

The first propagation path 16 and the second propagation path 26 comprise metal films 56, 58 evaporated respectively on the piezoelectric substrate 54. The metal films 56, 58 are electrically short-circuited. The metal film 56 of the first propagation path 16 is partially peeled off, thereby exposing the piezoelectric substrate 54 in an open area 60. Since the open area 60 is electrically open, the first propagation path 16 serves as an open propagation path. The remaining strip of the metal film 56 is electrically short-circuited. The second propagation path 26 is made up of the metal film 58 in its entirety, and hence serves as a short-circuited propagation path that is electrically short-circuited. The metal films 56, 58 are grounded in order to increase the accuracy with which physical properties of the object 52 are measured. The metal films 56, 58 may be made of any materials and are not limited to particular materials, however, the metal films 56, 58 should preferably be made of gold, which is chemically stable with respect to the object 52. Side walls 62 are disposed on the piezoelectric substrate 54 alongside the first propagation path 16 and the second propagation path 26. The side walls 62 extend from the input electrodes 12, 22 and toward the output electrodes 14, 24. The piezoelectric substrate 54 is not limited to any particular material. The piezoelectric substrate 54 may be in the form of a single substrate made of a piezoelectric material, or a substrate comprising a glass substrate with a thin film of piezoelectric material disposed on the glass substrate.

The first surface acoustic wave device 10 and the second surface acoustic wave device 20 are disposed parallel to each other on the piezoelectric substrate 54, which is mounted on a printed circuit board 64 by means of die bonding. Pads 66 disposed on the printed circuit board 64 are connected to the input electrodes 12, 22 and the output electrodes 14, 24 through bonding wires 68. An outer peripheral wall 70 is mounted on the peripheral edge of the printed circuit board 64. The peripheral walls 32a, 32b, the side walls 62, and the outer peripheral wall 70 jointly define a recess 72 therebetween, which is filled with an overcoat resin 74.

A method of manufacturing the liquid material property measuring apparatus 50 according to the first embodiment will be described below.

First, the input electrodes 12, 22, the output electrodes 14, 24, the first propagation path 16, and the second propagation path 26 are formed by photolithography on the piezoelectric substrate 54. The peripheral wall 32a is formed around the input electrodes 12, 22, the peripheral wall 32b is formed around the output electrodes 14, 24, and the side walls 62 are formed alongside the first propagation path 16 and the second propagation path 26, all of the walls being formed by a photosensitive resin (SU-8: photosensitive epoxy resin manufactured by Kayaku Microchem Co., Ltd.) which is used in photolithography.

Then, surfaces of the top plates 34a, 34b, which comprise glass substrates, are coated with an adhesive. The top plate 34a having been coated with the adhesive is bonded to the upper end of the peripheral wall 32a, and the top plate 34b similarly is bonded to the upper end of the peripheral wall 32b.

The piezoelectric substrate 54, with the input electrode 12, etc., formed thereon, is connected to the printed circuit board 64 by means of die bonding. Pads 66 on the printed circuit board 64 are connected to the input electrodes 12, 22 and the output electrodes 14, 24 through the bonding wires 68. Then, the outer peripheral wall 70 is formed using a thermosetting resin on the peripheral edge of the printed circuit board 64. Thereafter, the gaps 38a, 38b, which are formed by the top plates 34a, 34b and the piezoelectric substrate 54, are filled with a thixotropic underfilling agent, which serves as the sealing stiffeners 40a, 40b. Since the thixotropic underfilling agent is used as the sealing stiffeners 40a, 40b, the gaps 38a, 38b are filled with the sealing stiffeners 40a, 40b by means of capillary action. As a result, since the object 52 is prevented from coming into contact with the peripheral walls 32a, 32b, the peripheral walls 32a, 32b are prevented from being peeled off from the piezoelectric substrate 54, and hence the object 52 is prevented from being applied to the input electrodes 12, 22 and the output electrodes 14, 24. The recess 72, which is formed between the peripheral walls 32a, 32b, the side walls 62, and the outer peripheral wall 70, then is filled with the overcoat resin 74. In this manner, the liquid material property measuring apparatus 50 is manufactured.

The liquid material property measuring apparatus 50 measures physical properties of the object 52 as follows. The liquid material property measuring apparatus 50 is immersed in the object 52, and an oscillator, not shown, inputs identical signals to the input electrodes 12, 22. Based on the input signals, surface acoustic waves are excited by the input electrode 12, propagated over the first propagation path 16, and received by the output electrode 14. Similarly, based on the input signals, surface acoustic waves are excited by the input electrode 14, propagated over the second propagation path 26, and received by the output electrode 24. Output signals are generated from the surface acoustic waves, which are received by the output electrodes 14, 24, whereby the amplitude ratio and the phase difference of the output signals are detected. Physical properties of the object 52 are measured based on the detected amplitude ratio and the detected phase difference.

As described above, the liquid material property measuring apparatus 50 according to the first embodiment comprises the first surface acoustic wave device 10 having the first propagation path 16 disposed between the input electrode 12 and the output electrode 14, and the second surface acoustic wave device 20 having the second propagation path 26 disposed between the input electrode 22 and the output electrode 24, and wherein the second propagation path 26 has amplitude and phase characteristics different from those of the first propagation path 16. The liquid material property measuring apparatus 50 determines physical properties of the object 52, which is imposed on the first propagation path 16 and the second propagation path 26.

In the liquid material property measuring apparatus 50, the input electrodes 12, 22 are surrounded by the sealing member 30a defined by the peripheral wall 32a of the photosensitive resin disposed on the piezoelectric substrate 54, and the top plate 34a that covers the peripheral wall 32a. The sealing stiffener 40a is disposed on the piezoelectric substrate 54 in facing relation to the object 52 imposed on the piezoelectric substrate 54, such that the sealing stiffener 40a extends parallel to the wall 42a. The output electrodes 14, 24 are surrounded by the sealing member 30b defined by the peripheral wall 32b of the photosensitive resin disposed on the piezoelectric substrate 54, and the top plate 34b that covers the peripheral wall 32b. The sealing stiffener 40b is disposed on the piezoelectric substrate 54 in facing relation to the object 52 imposed on the piezoelectric substrate 54, such that the sealing stiffener 40b extends parallel to the wall 42b. The first surface acoustic wave device 10 and the second surface acoustic wave device 20 prevent the object 52 imposed on the piezoelectric substrate 54 from coming into contact with the peripheral walls 32a, 32b, prevent the peripheral walls 32a, 32b from being peeled off from the piezoelectric substrate 54, and prevent the piezoelectric substrate 54 from being applied to the input electrodes 12, 22 and the output electrodes 14, 24.

Figure 3:
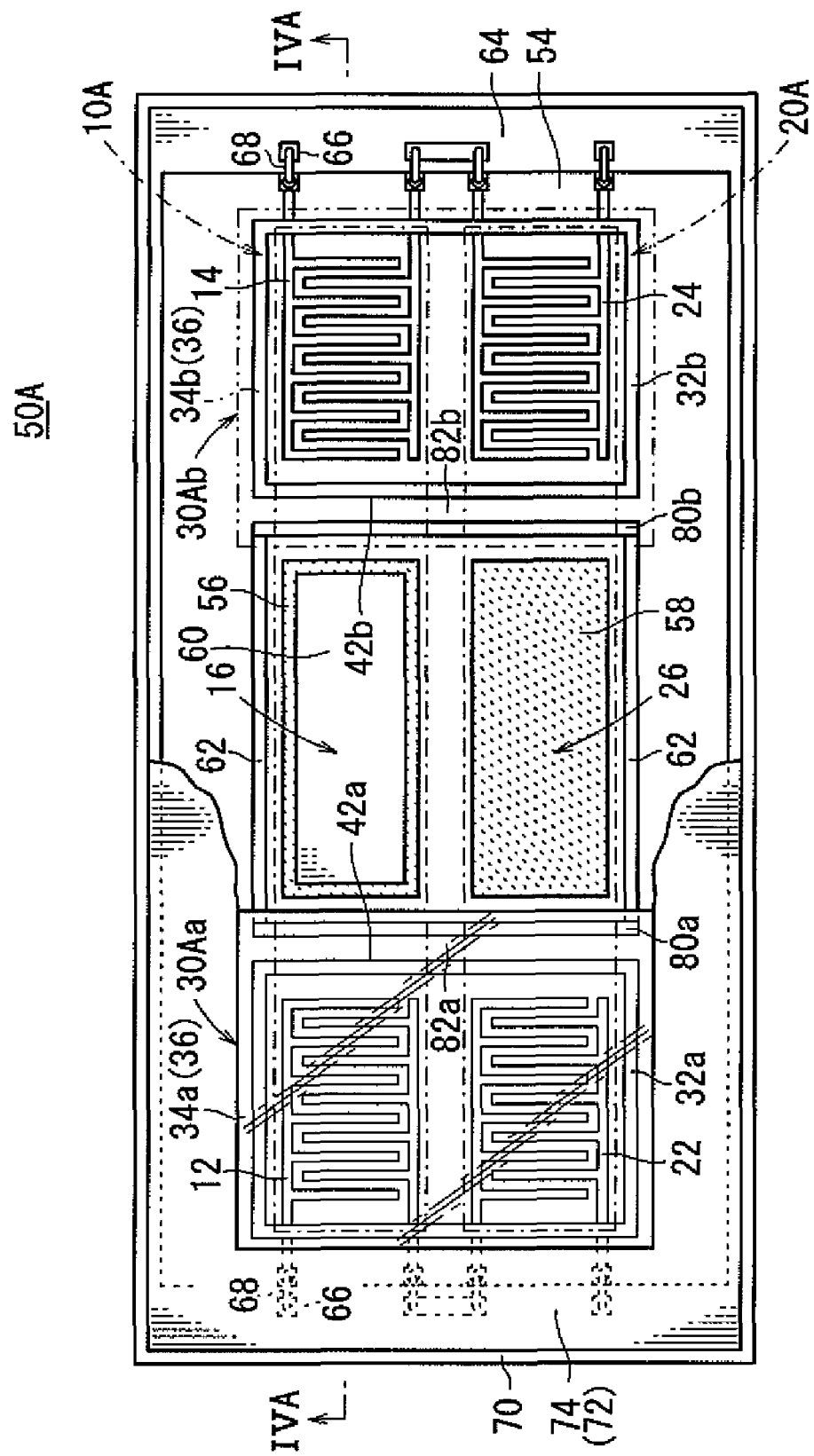
FIG. 3 is a plan view of a liquid material property measuring apparatus according to a second embodiment of the present invention.
Figure 4A:
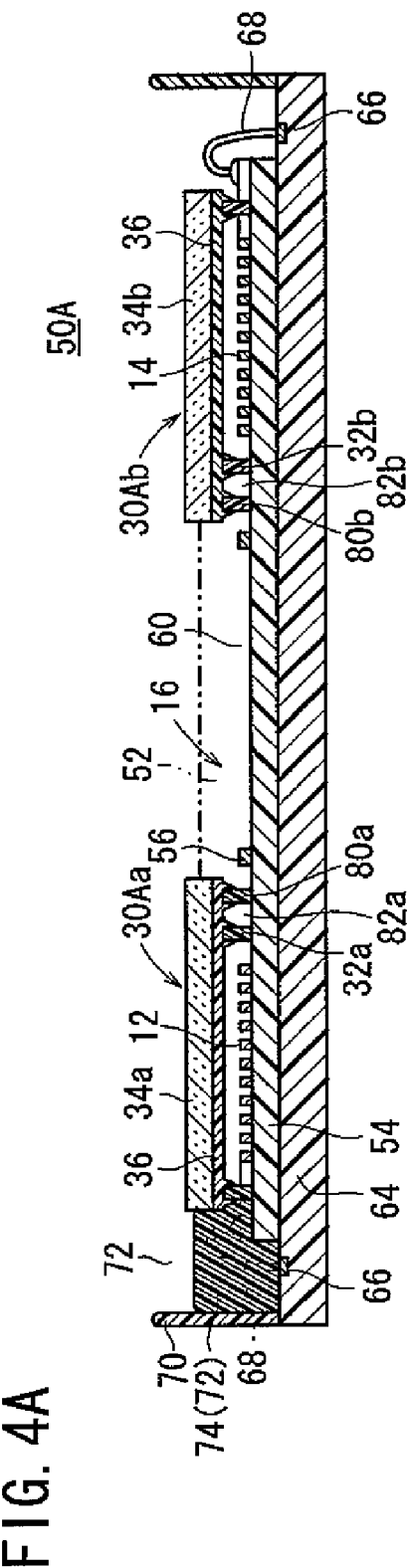
FIG. 4A is a partial end view taken along line IVA-IVA of FIG. 3.
Figure 4B:
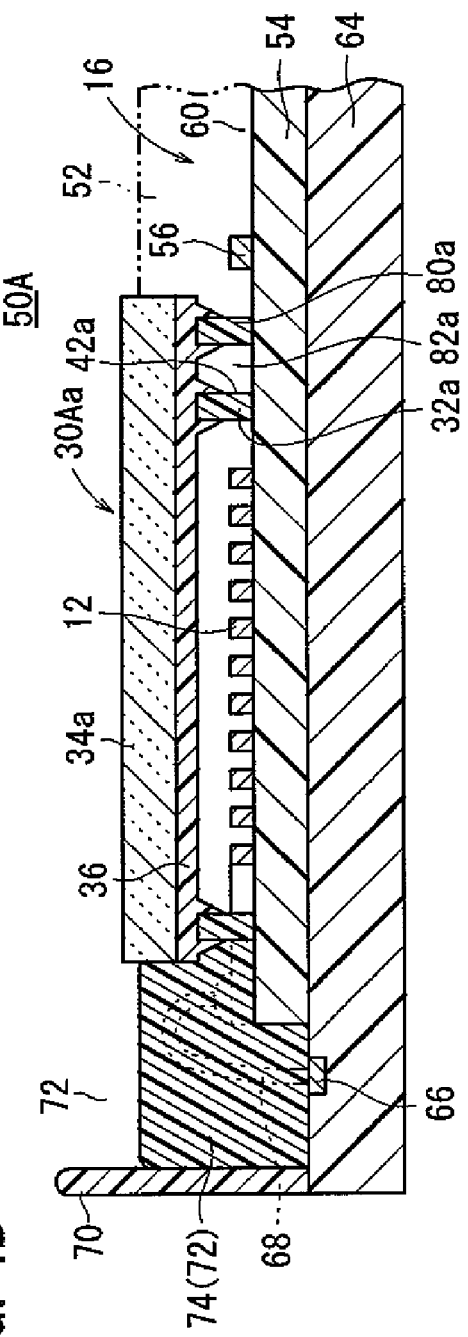
FIG. 4B is a partial enlarged view of FIG. 4A.

A liquid material property measuring apparatus 50A according to a second embodiment of the present invention will be described below. FIG. 3 is a plan view of the liquid material property measuring apparatus 50A according to the second embodiment of the present invention. FIG. 4A is a partial end view taken along line IVA-IVA of FIG. 1, and FIG. 4B is a partial enlarged view of FIG. 4A. Parts of the second embodiment which are identical to those of the first embodiment are denoted by identical reference characters, and such features will not be described in detail below.

The liquid material property measuring apparatus 50A differs from the liquid material property measuring apparatus 50 in that first walls 80a, 80b are added to sealing members 30Aa, 30Ab, and the peripheral walls 32a, 32b are not coated with the sealing stiffeners 40a, 40b. In the liquid material property measuring apparatus 50A, the first walls 80a, 80b, which are made of a photosensitive resin, are disposed on the piezoelectric substrate 54 in facing relation to the object 52 imposed on the piezoelectric substrate 54. Further, the sealing member 30Aa is constructed from the first wall 80*a*, the wall 42*a*, and the top plate 34*a*, and the sealing member 30Ab is constructed from the first wall 80*b*, the wall 42*b*, and the top plate 34*b*. The wall 42*a* and the first wall 80*a* that faces the wall 42*a*, as well as the wall 42*b* and the first wall 80*b* that faces the wall 42*b*, make up double protective walls, respectively, for protecting the object 52. Furthermore, the first propagation path 16 and the second propagation path 26 are surrounded by the first walls 80*a*, 80*b* and the side walls 62. The top plate 34*a*, which is coated on one surface thereof with the adhesive 36, is bonded to respective upper ends of the peripheral wall 32*a* and the first wall 80*a*. Also, the top plate 34*b*, which is coated on one surface thereof with the adhesive 36, is bonded to respective upper ends of the peripheral wall 32*b* and the first wall 80*b*. The top plate 34*a*, the peripheral wall 32*a*, the piezoelectric substrate 54, and the first wall 80*a* jointly define a closed space 82*a*, whereas the top plate 34*b*, the peripheral wall 32*b*, the piezoelectric substrate 54, and the first wall 80*b* jointly define another closed space 82*b*. Connections formed by the bonding wires 68 between the input electrodes 12, 22, the output electrodes 14, 24 and the printed circuit board 64, the outer peripheral wall 70 disposed on the printed circuit board 64, and the overcoat resin 74 are the same as in the first embodiment, and such features will not be described in detail below.

In the liquid material property measuring apparatus 50A, the input electrodes 12, 22 are surrounded by the sealing member 30Aa including the peripheral wall 32*a* of the photosensitive resin disposed on the piezoelectric substrate 54, the first wall 80*a* that faces the object 52 imposed on the piezoelectric substrate 54 and which extends parallel to a portion of the peripheral wall 32*a*, and the top plate 34*a* that covers the peripheral wall 32*a* and the first wall 80*a*. The output electrodes 14, 24 are surrounded by the sealing member 30Ab including the peripheral wall 32*a* of the photosensitive resin disposed on the piezoelectric substrate 54, the first wall 80*b* that faces the object 52 imposed on the piezoelectric substrate 54 and which extends parallel to a portion of the peripheral wall 32*b*, and the top plate 34*b* that covers the peripheral wall 32*b* and the first wall 80*b*.

In the liquid material property measuring apparatus 50A, the double protective walls prevent the object 52 from being applied to the input electrodes 12, 22 and the output electrodes 14, 24. Even if the first walls 80*a*, 80*b* become peeled off from the piezoelectric substrate 54, thereby allowing the object 52 to enter into the closed spaces 82*a*, 82*b*, a considerable period of time will be required before the peripheral walls 32*a*, 32*b* become peeled off from the piezoelectric substrate 54 by the object 52 that has entered into the closed spaces 82*a*, 82*b*. Therefore, a normal period of time can be maintained, during which the liquid material property measuring apparatus 50A can be used.

The liquid material property measuring apparatus 50A measures physical properties of the object 52 in the same manner as the first embodiment. Therefore, measurement of physical properties of the object 52 by means of the liquid material property measuring apparatus 50A will not be described in detail below.

Figure 5:
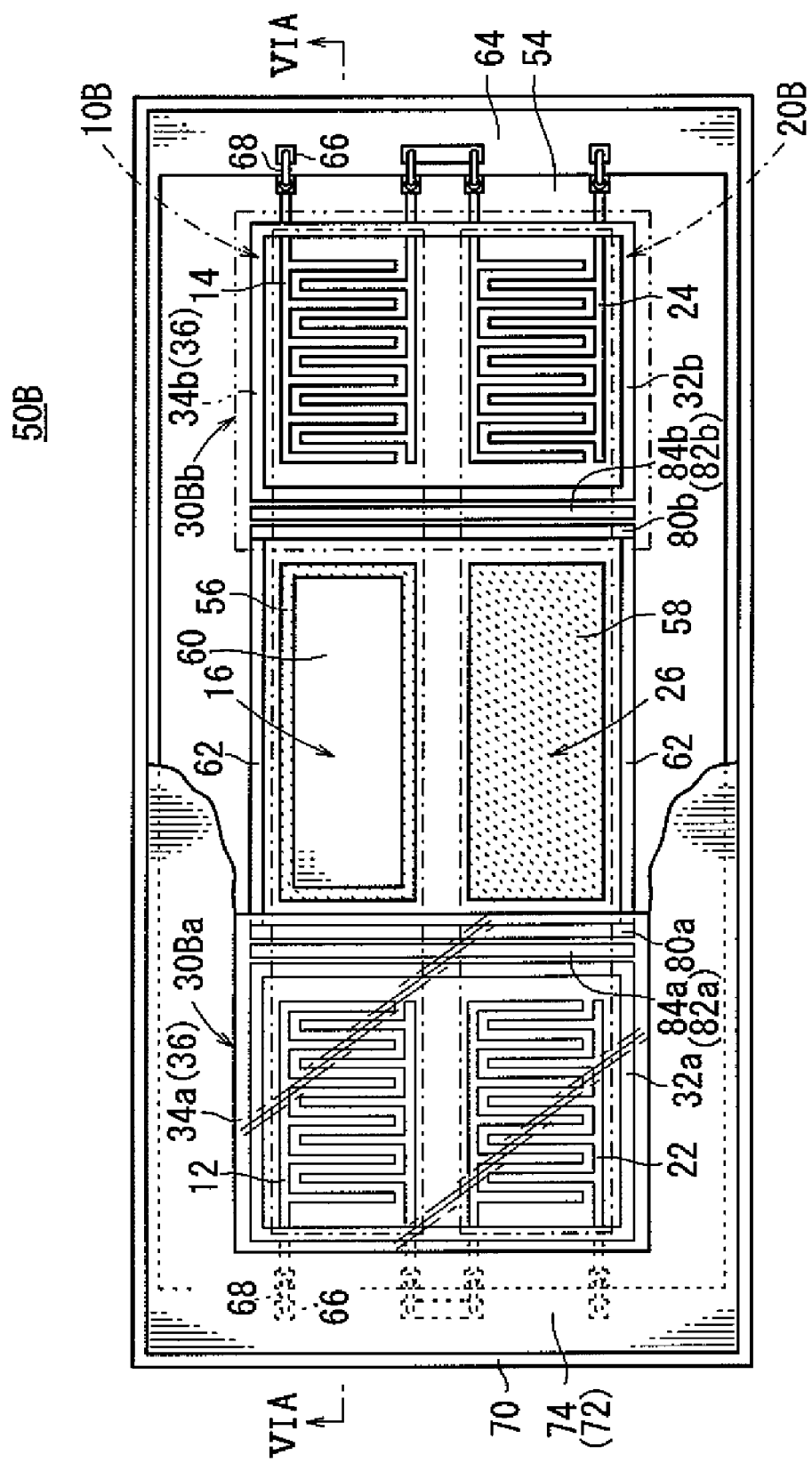
FIG. 5 is a plan view of a liquid material property measuring apparatus according to a third embodiment of the present invention.
Figure 6A:
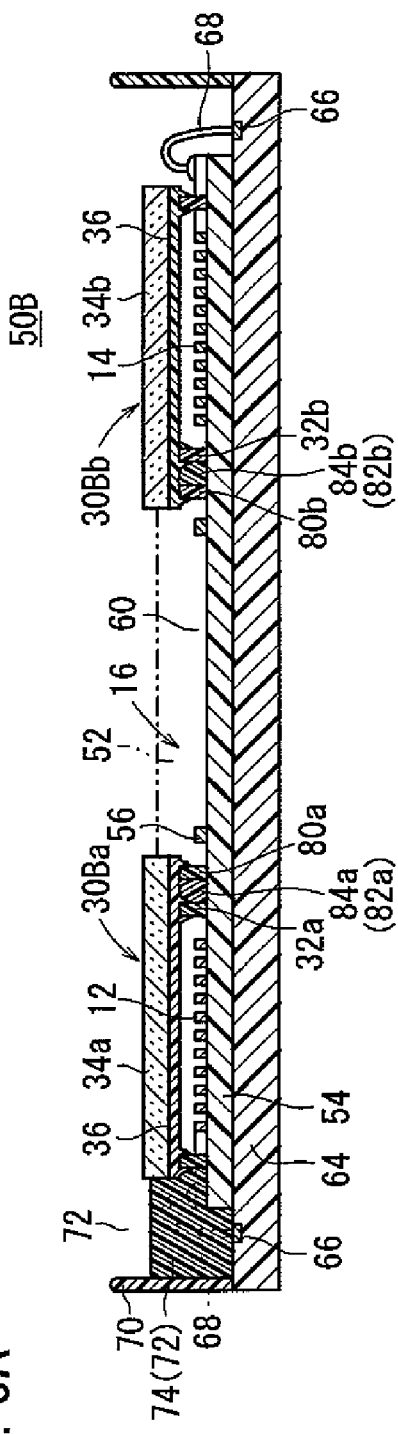
FIG. 6A is a partial end view taken along line VIA-VIA of FIG. 5.
Figure 6B:
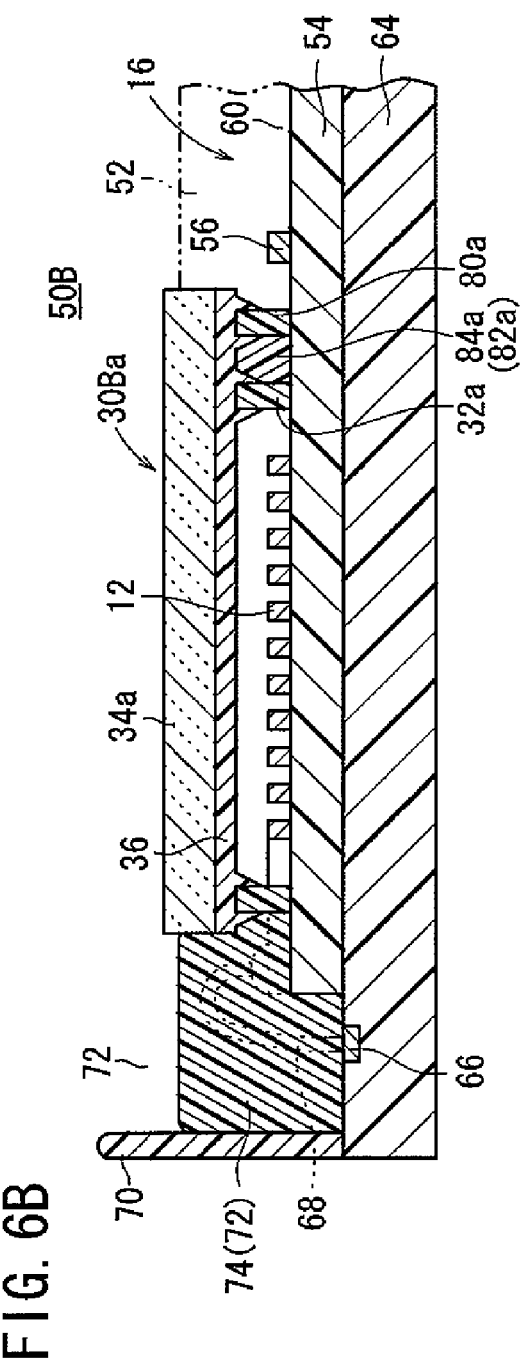
FIG. 6B is a partial enlarged view of FIG. 6A.

A liquid material property measuring apparatus 50B according to a third embodiment of the present invention will be described below. FIG. 5 is a plan view of the liquid material property measuring apparatus 50B according to the third embodiment of the present invention. FIG. 6A is a partial end view taken along line VIA-VIA of FIG. 5, and FIG. 6B is a partial enlarged view of FIG. 6A. Parts of the third embodiment which are identical to those of the first and second embodiments are denoted by identical reference characters, and such features will not be described in detail below.

The liquid material property measuring apparatus 50B differs from the liquid material property measuring apparatus 50 in that first walls 80*a*, 80*b* are added to sealing members 30Ba, 30Bb. In the liquid material property measuring apparatus 50B, the first walls 80*a*, 80*b*, which are made of a photosensitive resin, are disposed on the piezoelectric substrate 54 in facing relation to the object 52 imposed on the piezoelectric substrate 54. The sealing member 30Ba is constructed from the first wall 80*a*, the wall 42*a*, and the top plate 34*a*, whereas the sealing member 30Bb is constructed from the first wall 80*b*, the wall 42*b*, and the top plate 34*b*. Furthermore, the first propagation path 16 and the second propagation path 26 are surrounded by the first walls 80*a*, 80*b* and the side walls 62. The top plate 34*a*, which is coated on one surface thereof with the adhesive 36, is bonded to respective upper ends of the peripheral wall 32*a* and the first wall 80*a*. The top plate 34*b*, which is coated on one surface thereof with the adhesive 36, is bonded to respective upper ends of the peripheral wall 32*b* and the first wall 80*b*. The top plate 34*a*, the peripheral wall 32*a*, the piezoelectric substrate 54, and the first wall 80*a* jointly define a closed space 82*a*, whereas the top plate 34*b*, the peripheral wall 32*b*, the piezoelectric substrate 54, and the first wall 80*b* jointly define another closed space 82*b*. The closed space 82*a* and the closed space 82*b* are filled respectively with sealing stiffeners 84*a*, 84*b*, which comprise a thixotropic underfilling agent, in order to more reliably prevent the object 52 from being applied to the input electrodes 12, 22 and the output electrodes 14, 24.

Connections by the bonding wires 68 between the input electrodes 12, 22, the output electrodes 14, 24 and the printed circuit board 64, the outer peripheral wall 70 disposed on the printed circuit board 64, and the overcoat resin 74 are the same as in the first embodiment, and such features will not be described in detail below. The liquid material property measuring apparatus 50B measures physical properties of the object 52 in the same manner as the first embodiment. Therefore, measurement of physical properties of the object 52 by means of the liquid material property measuring apparatus 50B will not be described in detail below.

Figure 7:
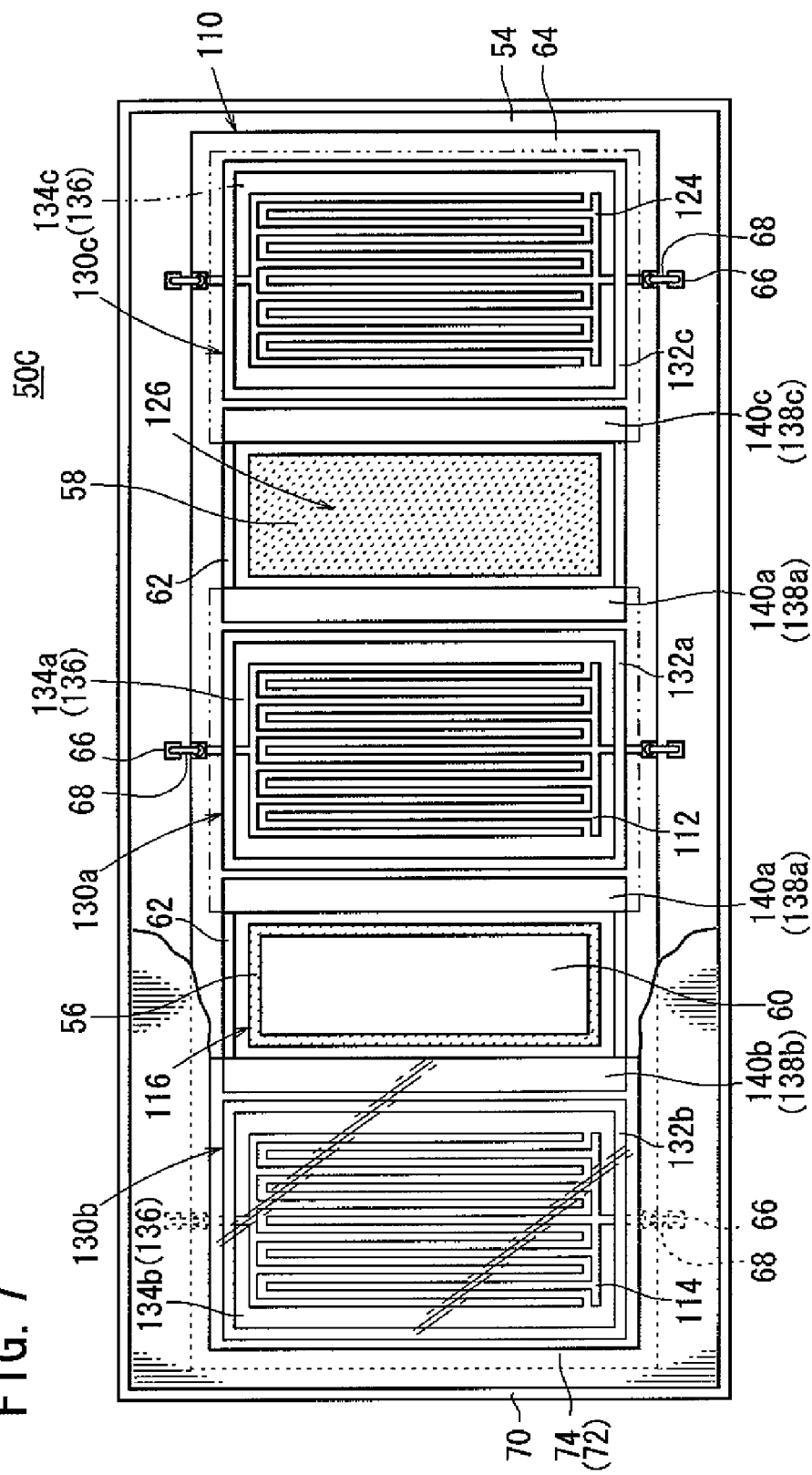
FIG. 7 is a plan view of a liquid material property measuring apparatus according to a fourth embodiment of the present invention.

A liquid material property measuring apparatus 50C according to a fourth embodiment of the present invention will be described below. FIG. 7 is a plan view of the liquid material property measuring apparatus 50C according to the fourth embodiment of the present invention. In the first through third embodiments described above, the first surface acoustic wave device 10 and the second surface acoustic wave device 20 include respective input electrodes 12 and respective output electrodes 14. However, the liquid material property measuring apparatus 50C has a single input electrode. Other parts of the fourth embodiment which are identical to those of the first embodiment are denoted by identical reference characters, and such features will not be described in detail below.

The liquid material property measuring apparatus 50C comprises a surface acoustic wave device having one input electrode 112 and output electrodes 114, 124, a first transmission path 116 disposed as an open transmission path between the input electrode 112 and the output electrode 114, and a second transmission path 126 disposed as a short-circuited transmission path between the input electrode 112 and the output electrode 124.

The input electrode 112 is sealed by a sealing member 130*a*, the output electrode 114 is sealed by a sealing member 130b, and the output electrode 124 is sealed by a sealing member 130c, for preventing the object 52 from being applied to the comb-tooth electrodes when physical properties of the object 52 are measured.

The sealing member 130a comprises a peripheral wall 132a and a top plate 134a. The peripheral wall 132a is disposed on the piezoelectric substrate 54 in surrounding relation to the input electrode 112. The top plate 134a is bonded by an adhesive 136 to the upper end of the peripheral wall 132a. The top plate 134a is bonded to the upper end of the peripheral wall 132a, substantially parallel to the piezoelectric substrate 54. The top plate 134a extends toward the output electrodes 114, 124, with a gap 138a being defined between one end of the top plate 134a and the piezoelectric substrate 54. The gap 138a is filled with a sealing stiffener 140a, which is applied to a surface of the peripheral wall 132a that faces the object 52 imposed on the piezoelectric substrate 54. Similar to the sealing member 130a, the sealing member 130b comprises a peripheral wall 132b and a top plate 134b. A gap 138b is filled with a sealing stiffener 140b, which is applied to the peripheral wall 132b. Similar to the sealing member 130a, the sealing member 130c comprises a peripheral wall 132c and a top plate 134c. A gap 138c is filled with a sealing stiffener 140c, which is applied to the peripheral wall 132c.

Connections by means of the bonding wires 68 between the input electrode 112, the output electrodes 114, 124 and the printed circuit board 64, the outer peripheral wall 70 disposed on the printed circuit board 64, and the overcoat resin 74 are the same as in the first embodiment, and such features will not be described in detail below.

The liquid material property measuring apparatus 50C measures physical properties of the object 52 as follows. The liquid material property measuring apparatus 50C is immersed in the object 52, and an oscillator, not shown, inputs an electric signal to the input electrode 112. Based on the input signal, identical surface acoustic waves are excited from both sides of the input electrode 112, one of which is propagated over the first propagation path 116 and received by the output electrode 114, and the other of which is propagated over the second propagation path 126 and received by the output electrode 124.

Output signals are generated from the surface acoustic waves received by the output electrodes 114, 124, and the amplitude ratio and phase difference of the output signals are detected. Physical properties of the object 52 are measured based on the detected amplitude ratio and the detected phase difference.

The liquid material property measuring apparatus 50C has a construction similar to the liquid material property measuring apparatus 50 according to the first embodiment, except that the liquid material property measuring apparatus 50C has only a single input electrode. However, it will be understood that the liquid material property measuring apparatus 50C may be constructed similar to the liquid material property measuring apparatus 50A according to the second embodiment, except for having a single input electrode. Also, the liquid material property measuring apparatus 50C may be constructed similar to the liquid material property measuring apparatus 50B according to the third embodiment, except for having a single input electrode.

Figure 8:
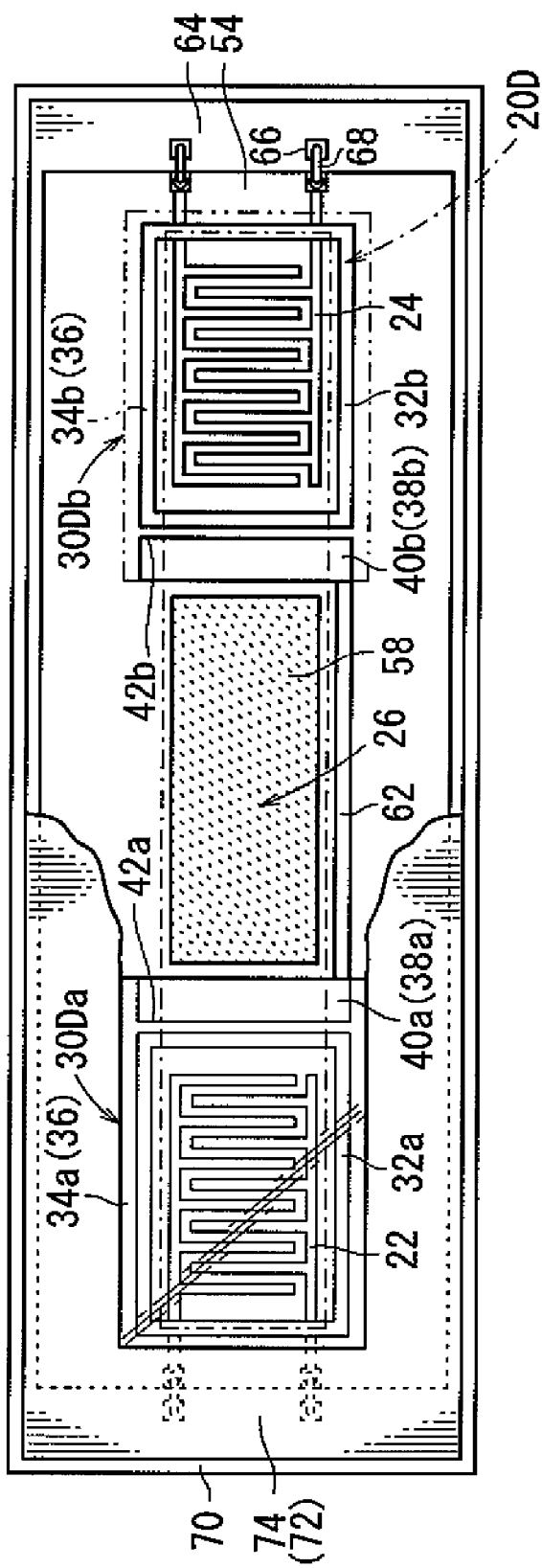
FIG. 8 is a plan view of a liquid material property measuring apparatus according to a fifth embodiment of the present invention.

A liquid material property measuring apparatus 50D according to a fifth embodiment of the present invention will be described below. FIG. 8 is a plan view of the liquid material property measuring apparatus 50D according to the fifth embodiment of the present invention. In the first embodiment described above, the liquid material property measuring apparatus 50 includes the first surface acoustic wave device 10 and the second surface acoustic wave device 20. However, the liquid material property measuring apparatus 50D also comprises a second surface acoustic wave device 20D. Other parts of the fifth embodiment, which are identical to those of the first embodiment, are denoted by identical reference characters, and such features will not be described in detail below.

In the liquid material property measuring apparatus 50D, the input electrode 22 is surrounded by a sealing member 30Da, which comprises the peripheral wall 32a of the photosensitive resin disposed on the piezoelectric substrate 54, and the top plate 34a that covers the peripheral wall 32a. The sealing stiffener 40a is disposed between the object 52 and the wall portion 42a of the peripheral wall 32a, which faces the object 52 imposed on the piezoelectric substrate 54. The output electrode 24 is surrounded by a sealing member 30Db, which comprises the peripheral wall 32b of the photosensitive resin disposed on the piezoelectric substrate 54, and the top plate 34b that covers the peripheral wall 32b. The sealing stiffener 40b is disposed between the object 52 and the wall portion 42b of the peripheral wall 32b, which faces the object 52 imposed on the piezoelectric substrate 54. The second surface acoustic wave device 20D prevents the object 52 from coming into contact with the peripheral walls 32a, 32b, prevents the peripheral walls 32a, 32b from being peeled off from the piezoelectric substrate 54, and prevents the piezoelectric substrate 54 from being applied to the input electrode 22 and the output electrode 24. Connections by means of the bonding wires 68 between the input electrode 12, the output electrode 24 and the printed circuit board 64, the outer peripheral wall 70 disposed on the printed circuit board 64, and the overcoat resin 74 are the same as in the first embodiment, and such features will not be described in detail below.

The liquid material property measuring apparatus 50D measures physical properties of the object 52 as follows. The liquid material property measuring apparatus 50D is immersed in the object 52, and an oscillator, not shown, inputs an electric signal to the input electrode 22. Surface acoustic waves are excited from the input electrode 22, propagated over the second propagation path 26, and are received by the output electrode 24. An output signal is generated from the surface acoustic waves received by the output electrodes 24, and the amplitude ratio and phase difference of the output signal and the electric signal from the oscillator are detected. Based on the detected amplitude ratio and phase difference, the density, viscosity, and the immobilized quantity of the object 52 are measured as physical properties of the object 52.

The liquid material property measuring apparatus 50D may be constructed so as to include a double protective wall, by providing a first wall of photosensitive resin formed between the wall 42a of the peripheral wall 32a and the object 52 imposed on the piezoelectric substrate 54, and a second wall of photosensitive resin formed between the wall 42b of the peripheral wall 32b and the object 52 imposed on the piezoelectric substrate 54, similar to the first embodiment. The liquid material property measuring apparatus 50D may also be constructed by filling, with sealing stiffeners, the closed space defined by the top plate 34a, the peripheral wall 32a, the piezoelectric substrate 54, and the first wall, and the closed space defined by the top plate 34b, the peripheral wall 32b, the piezoelectric substrate 54, and the first wall, similar to the third embodiment.

Physical properties of the object, which are measured by the liquid material property measuring apparatus 50, are not limited to relative permittivity, electric conductivity and density, as referred to above. The liquid material property measuring apparatus 50 also can measure the viscosity of the measurement object, for example.

The object to be measured is not limited to any particular substances, but may contain at least one liquid. The object to be measured may contain either a pure liquid or a mixed liquid. The present invention is particularly effective in measuring the physical properties of alcohols, such as methanol, ethanol, etc. Even if the object to be measured contains antigens, antibodies, bacteria, etc., therein, the physical properties of the object can be measured.

If the object to be measured contains charged bacteria, then the content percentage of such bacteria can be measured by measuring the electric conductivity of the object. If the object to be measured contains bacteria charged at different polarities, then the type of bacteria that is dominant in the object can be identified by measuring the electric conductivity of the object. If bacteria are applied to the propagation path on which the object to be measured is imposed, then an increase or decrease in the applied bacteria can be detected by measuring the density and viscosity of the object.

Furthermore, a mass change or a viscosity change can be detected, in a case where a protein is adsorbed by the surface of a metal film. More specifically, the adsorbed amount of protein and the type of the adsorbed protein can be detected by measuring the amplitude and phase of a surface acoustic wave, which is propagated over the metal film.

If an antibody is immobilized on the surface of a metal film and an antigen solution is imposed thereon, then a mass change or a viscosity change can be detected by binding of the antigen and the antibody. More specifically, the amount of the imposed antigen can be detected by measuring the amplitude and phase of a surface acoustic wave, which is propagated over the metal film. It is therefore evident that if an antigen is immobilized on the surface of a metal film and an antibody solution is imposed thereon, then the amount of the imposed antibody can be detected.

The present invention is not limited to the above embodiments, but various arrangements may be adopted therein without departing from the scope of the invention.

The invention claimed is:

1. A surface acoustic wave device having electrodes disposed on a piezoelectric substrate, comprising:
   a sealing member having a peripheral wall disposed on the piezoelectric substrate in surrounding relation to the electrodes, and a top plate covering the peripheral wall; and
   a sealing stiffener being in facing relation to a liquid material imposed on the piezoelectric substrate and which extends parallel to a wall portion of the peripheral wall facing the liquid material between the wall portion and the liquid material.

2. A surface acoustic wave device having electrodes disposed on a piezoelectric substrate, comprising a sealing member sealing the electrodes,
   wherein the sealing member has a peripheral wall disposed on the piezoelectric substrate in surrounding relation to the electrodes, a first wall being in facing relation to a liquid material imposed on the piezoelectric substrate and which extends parallel to a wall portion of the peripheral wall facing the liquid material between the wall portion and the liquid material, and a top plate covering the peripheral wall and the first wall.

3. A surface acoustic wave device according to claim 2, further comprising:
   a sealing stiffener filling a space between the first wall and the wall portion of the peripheral wall that faces the first wall.

4. A surface acoustic wave device according to claim 1, wherein the peripheral wall is made of a photosensitive resin.

5. A surface acoustic wave device according to claim 2, wherein the peripheral wall is made of a photosensitive resin.

6. A liquid material property measuring apparatus including a surface acoustic wave device according to claim 4, wherein the electrodes include an input electrode—and an output electrode, each of which is sealed by the sealing member, and wherein the liquid material property measuring apparatus determines physical properties of the liquid material, which is imposed on a transmission path disposed between the input electrode and the output electrode.

7. A liquid material property measuring apparatus including a surface acoustic wave device according to claim 5, wherein the electrodes include an input electrode and an output electrode, each of which is sealed by the sealing member, and wherein the liquid material property measuring apparatus determines physical properties of the liquid material, which is imposed on a transmission path disposed between the input electrode and the output electrode.

8. A surface acoustic wave device according to claim 1, wherein the electrodes include an input electrode and an output electrode disposed on the piezoelectric substrate,
   the sealing member includes:
   an input side sealing member having an input side peripheral wall disposed on the piezoelectric substrate in surrounding relation to the input electrode and an input side top plate covering the input side peripheral wall; and
   an output side sealing member having an output side peripheral wall disposed on the piezoelectric substrate in surrounding relation to the output electrode and an output side top plate covering the output side peripheral wall, and
   the sealing stiffener includes:
   an input side sealing stiffener being in facing relation to the liquid material imposed between the input side sealing member and the output side sealing member on the piezoelectric substrate and which extends parallel to a wall portion of the input side peripheral wall facing the liquid material between the wall portion of the input side peripheral Wall facing the liquid material and the liquid material; and
   an output side sealing stiffener being in facing relation to the liquid material, and which extends parallel to a wall portion of the output side peripheral wall facing the liquid material between the wall portion of the output side peripheral wall facing the liquid material and the liquid material.

9. A surface acoustic wave device according to claim 2, wherein the electrodes include an input electrode and an output electrode disposed on the piezoelectric substrate,
   the sealing member includes an input side sealing member sealing the input electrode and an output side sealing member sealing the output electrode,
   the input side sealing member has an input side peripheral wall disposed on the piezoelectric substrate in surrounding relation to the input electrode, an input side first wall being in facing relation to the liquid material imposed between the input side sealing member and the output side sealing member on the piezoelectric substrate and which extends parallel to a wall portion of the input side peripheral wall facing the liquid material between the wall portion of the input side peripheral wall facing the liquid material and the liquid material, and an input side top plate covering the input side peripheral wall and the input side first wall, and the output side sealing member has an output side peripheral wall disposed on the piezoelectric substrate in surrounding relation to the output electrode, an output side first wall being in facing relation to the liquid material and which extends parallel to a wall portion of the output side peripheral wall facing the liquid material between the wall portion of the output side peripheral wall facing the liquid material and the liquid material, and an output side top plate covering the output side peripheral wall and the output side first wall.

10. A surface acoustic wave device according to claim 9, wherein sealing stiffeners fill a space between the input side first wall and the wall portion of the input peripheral wall that faces the input side first wall, and a space between the output side first wall and the wall portion of the output peripheral wall that faces the output side first wall, respectively.

* * * * *